United States Patent
Bruin et al.

(10) Patent No.: US 9,962,508 B2
(45) Date of Patent: *May 8, 2018

(54) DRUG DELIVERY INHALER DEVICES

(71) Applicant: Clement Clarke International Ltd., Essex (GB)

(72) Inventors: Ronald Bruin, Essex (GB); David Spencer, Essex (GB); Mark Sanders, Bedfordshire (GB)

(73) Assignee: CLEMENT CLARKE INTERNATIONAL, LTD., Essex (GB)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/239,406

(22) Filed: Aug. 17, 2016

(65) Prior Publication Data
US 2016/0354565 A1 Dec. 8, 2016

Related U.S. Application Data

(63) Continuation of application No. 13/749,203, filed on Jan. 24, 2013, now Pat. No. 9,427,534.

(51) Int. Cl.
*A61M 15/00* (2006.01)
*A61M 11/04* (2006.01)
*A61M 16/00* (2006.01)

(52) U.S. Cl.
CPC .......... *A61M 15/009* (2013.01); *A61M 11/04* (2013.01); *A61M 15/0021* (2014.02);
(Continued)

(58) Field of Classification Search
CPC .......... A61D 7/00; A61D 7/04; A61J 7/0481; A61M 11/006; A61M 11/007;
(Continued)

(56) References Cited

U.S. PATENT DOCUMENTS

| 3,732,864 A | 5/1973 | Thompson et al. |
| 4,291,688 A | 9/1981 | Kistler |

(Continued)

FOREIGN PATENT DOCUMENTS

| EP | 0 014 814 A1 | 9/1980 |
| EP | 1 044 647 A1 | 10/2000 |

(Continued)

OTHER PUBLICATIONS

Clement Clarke website—[online] [retrieved Jul. 30, 2013]. Retrieved from the Internet: <URL: file://R:/Marketing/3.%20Website/Flo-tone%20website/Flo-Tone%20Website%20v . . . > (Aug. 28, 2012) 5 pages.

(Continued)

*Primary Examiner* — Annette Dixon
(74) *Attorney, Agent, or Firm* — Womble Bond Dickinson (US) LLP

(57) ABSTRACT

An adapter for fitting to a drug delivery device, the adapter including: an outlet for communication with the mouth of a patient; an air flow path through the adapter along which air is drawn to the outlet by inhalation by the patient; an inlet adapted for connection to a mouthpiece of the drug delivery device; and an air flow rate indicator operable to indicate when the air flow rate along the air flow path is at or above a predetermined minimum level suitable for delivery of the drug to the patient. A drug delivery device having, in its body, an air flow rate indicator operable to indicate when the air flow rate along the air flow path is at or above a predetermined minimum level suitable for delivery of the drug to the patient.

20 Claims, 4 Drawing Sheets

(52) U.S. Cl.
CPC . *A61M 15/0086* (2013.01); *A61M 2016/0033* (2013.01); *A61M 2205/3334* (2013.01); *A61M 2205/581* (2013.01); *A61M 2205/583* (2013.01)

(58) Field of Classification Search
CPC ...... A61M 11/04; A61M 11/06; A61M 11/08; A61M 15/00; A61M 15/0003; A61M 15/0005; A61M 15/0015; A61M 15/0016; A61M 15/0018; A61M 15/0021; A61M 15/0065; A61M 15/0066; A61M 15/0068; A61M 15/0073; A61M 15/0076; A61M 15/008; A61M 15/0086; A61M 15/009; A61M 15/0091; A61M 15/0095; A61M 16/06; A61M 16/08; A61M 16/0816; A61M 16/0833; A61M 16/10; A61M 16/14; A61M 16/20; A61M 16/208; A61M 2005/1405; A61M 2016/0021; A61M 2016/0027; A61M 2016/003; A61M 2016/0033; A61M 2016/0036; A61M 2016/0039; A61M 2016/0042; A61M 2205/0233; A61M 2205/13; A61M 2205/14; A61M 2205/183; A61M 2205/276; A61M 2205/3306; A61M 2205/332; A61M 2205/3334; A61M 2205/3368; A61M 2205/3375; A61M 2205/35; A61M 2205/3561; A61M 2205/43; A61M 2205/44; A61M 2205/50; A61M 2205/502; A61M 2205/52; A61M 2205/581; A61M 2205/582; A61M 2205/583; A61M 2205/59; A61M 2205/8206; A61M 2207/00; A61N 7/00; G06M 1/028; G06M 1/041; A61B 5/08; A61B 5/087; A61B 5/0875; A61B 5/091; A61B 5/7242; A61B 8/0875; A61B 5/0876; A63B 23/18; Y10S 128/905; Y10T 29/04
USPC ............ 128/200.14, 200.23, 200.24, 202.17, 128/202.22, 203.12, 203.14, 203.15, 128/203.23, 203.24, 203.28, 204.23, 128/205.23, 205.24, 205.25, 206.21, 128/207.15, 905
See application file for complete search history.

(56) References Cited

U.S. PATENT DOCUMENTS

| | | | |
|---|---|---|---|
| 4,421,120 A | 12/1983 | Edwards, Jr. et al. | |
| 5,042,467 A | 8/1991 | Foley | |
| 5,284,133 A | 2/1994 | Burns et al. | |
| 5,363,842 A | 11/1994 | Mishelevich et al. | |
| 5,617,844 A | 4/1997 | King | |
| 5,758,638 A | 6/1998 | Kreamer | |
| 5,865,172 A | 2/1999 | Butler et al. | |
| 5,970,973 A | 10/1999 | Gonda et al. | |
| 6,014,972 A | 1/2000 | Sladek | |
| 6,039,042 A | 3/2000 | Sladek | |
| 9,427,534 B2 * | 8/2016 | Bruin ................ A61M 15/0021 |
| 2008/0017190 A1 | 1/2008 | Anandampillai et al. | |
| 2013/0151162 A1 | 6/2013 | Harris et al. | |

FOREIGN PATENT DOCUMENTS

| | | | | |
|---|---|---|---|---|
| EP | 1338296 | | 8/2003 | |
| EP | 1407794 | | 4/2004 | |
| FR | 2763507 A1 | | 11/1998 | |
| GB | 1392945 | | 5/1975 | |
| GB | 2 104 385 A | | 3/1983 | |
| GB | 2340407 | | 2/2000 | |
| GB | 2372704 | | 9/2002 | |
| GB | 2490770 | | 11/2012 | |
| GB | 2490770 A | * | 11/2012 | .......... A61M 15/009 |
| WO | WO-88/02267 | | 4/1988 | |
| WO | WO-92/07599 | | 5/1992 | |
| WO | WO 97/30632 A1 | | 8/1997 | |
| WO | WO-01/07107 | | 2/2001 | |
| WO | WO-03/013634 | | 2/2003 | |
| WO | WO-03/059423 | | 7/2003 | |
| WO | WO-03/097142 | | 11/2003 | |

OTHER PUBLICATIONS

Corrigan, C.; "Asthma therapy: there are guidelines, and then there is real life . . . ;" Primary Care Respiratory Journal, vol. 20, No. 1; dated Feb. 15, 2011; retrieved on January 30, 2013 from <http://www.thepcrj.org/journ/vol20/20_1_13_14.pdf>.

Hardwell, A., et al.; "Technique training does not improve the ability of most patients to use pressurized metered-dose inhalers (pMDIs);" Primary Care Respiratory Journal, vol. 20, No. 1; dated Dec. 6, 2011; retrieved on Jan. 30, 2013 from <www.thepcrj.org/journ/vol20/20_1_92_96.pdf>.

In-Check™ Flo-Tone (exhibition panel) Clement Clarke International, Issue Aug. 2012 (Aug. 16, 2012) 2 pages.

Lavorini, F., et al.; "The ADMIT series—Issues in Inhalation Therapy. 6) Training tools for inhalation devices;" Primary Care Respiratory Journal, vol. 19, No. 4; dated Nov. 3, 2010; retrieved on Jan. 30, 2013 from <http://www.thepcrj.org/journ/vol19/19_4_335_341.pdf>.

New Flo-Tone pMDI attachment, audible coaching signal at correct flow (promotional card), Clement Clarke International (Aug. 2012) 1 page.

* cited by examiner

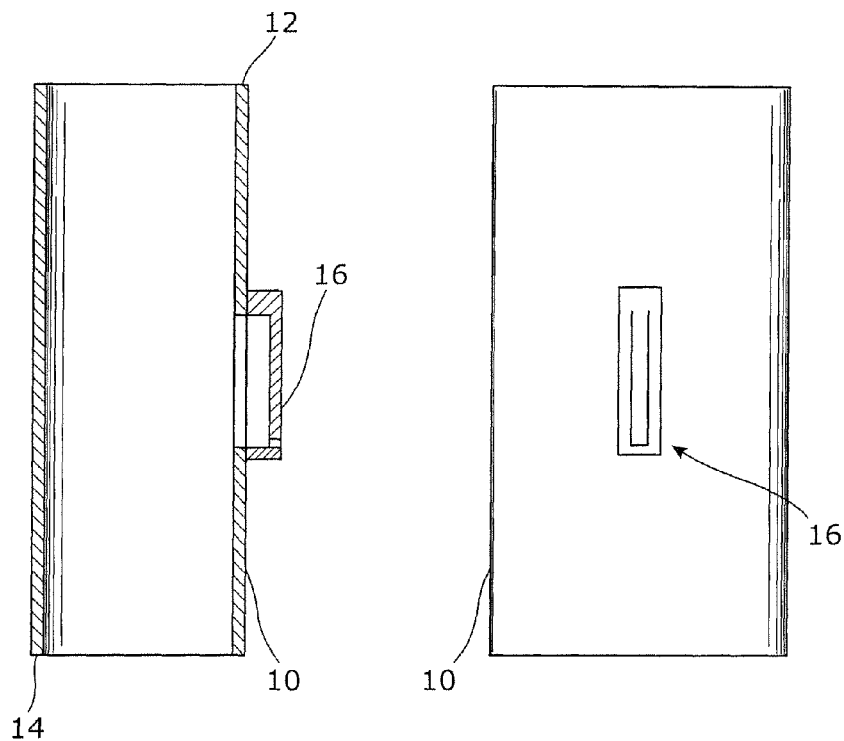
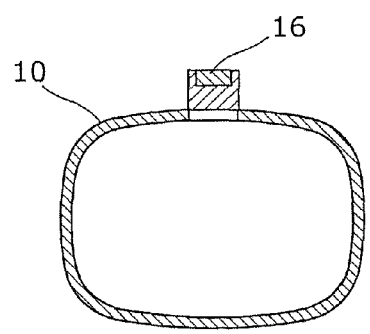
Fig. 1  Fig. 2
Fig. 3

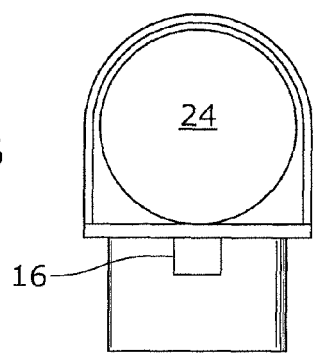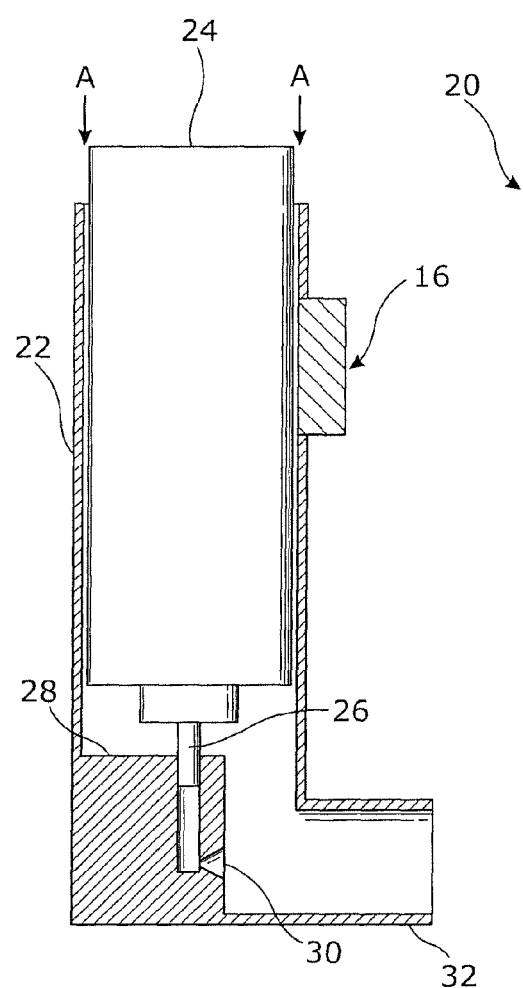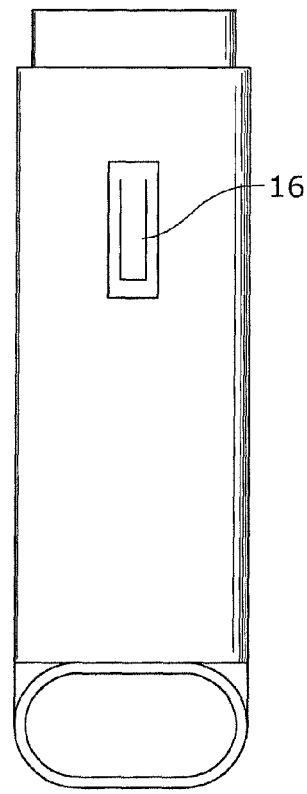
Fig. 6
Fig. 4 Fig. 5

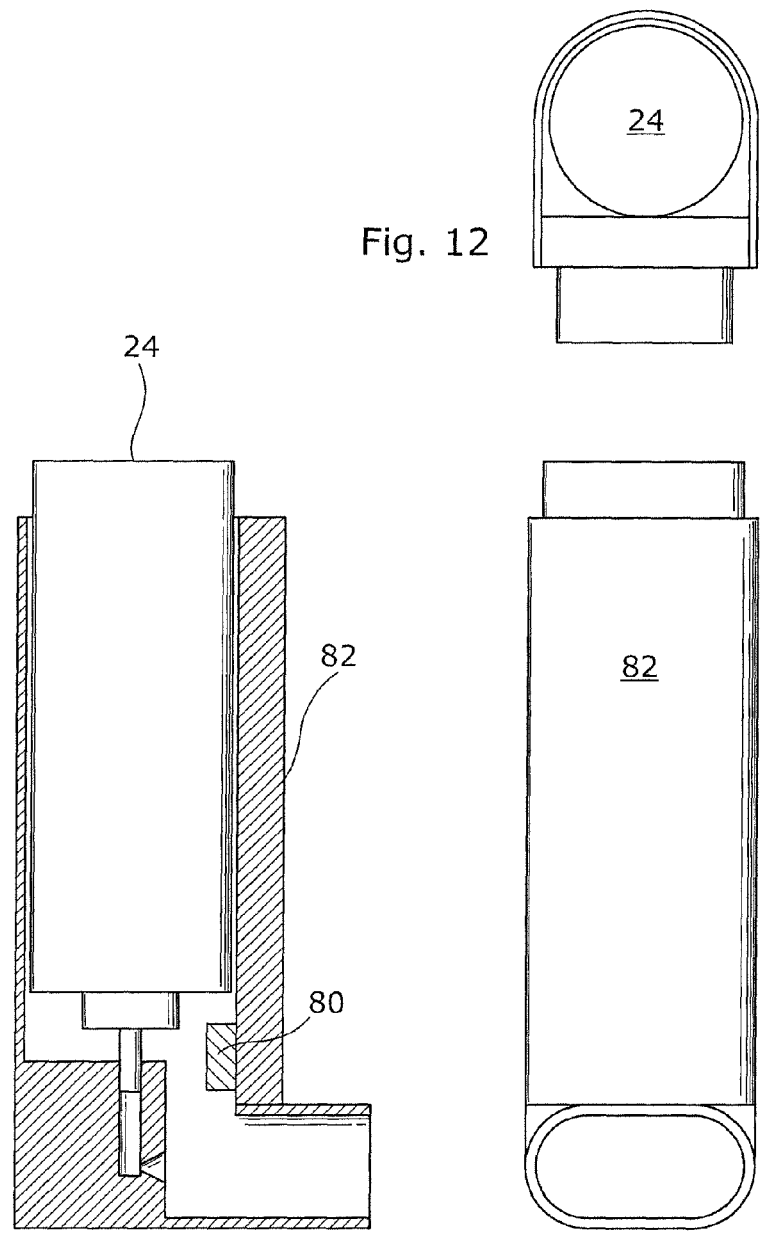

DRUG DELIVERY INHALER DEVICES

CROSS REFERENCE TO RELATED APPLICATIONS

This application is a continuation of U.S. patent application Ser. No. 13/749,203, filed Jan. 24, 2013, now U.S. Pat. No. 9,427,534, which is entitled "DRUG DELIVERY INHALER DEVICES", which application is incorporated herein by reference in its entirety.

BACKGROUND TO THE INVENTION

Field of the Invention

The present invention relates to drug delivery inhaler devices, such as pressurised metered dose inhaler (pMDI) devices and dry powder inhaler (DPI) devices and adapters for fitting to such drug delivery inhaler devices. The invention also relates to methods of operation of such devices and adapters. Of particular interest in this invention is the provision of means for improving patient compliance with such devices.

Related Art

GB-A-2372704 discloses a device, such as a spirometer, for determining the respiratory flow rate of a patient. The device includes two reeds adapted to generate an audible signal at different air flow speeds through the device. The first reed generates an audible signal of a first pitch when the air flow reaches a predetermined minimum. The second reed generates an audible signal of a second pitch when the air flow reaches a predetermined maximum. Thus, the patient is informed when the air flow is within a desirable range, between the predetermined minimum and maximum.

Lavorini et al (2010) [F. Lavorini, M. L. Levy, C. Corrigan and Graham Crompton, "The ADMIT series—issues in inhalation therapy. 6) Training tools for inhalation devices" Primary Care Respiratory Journal (2010) 19(4) 335-341] set out a review of training tools for inhalation devices, including the device disclosed in GB-A-2372704, referred to as the "2Tone" trainer. Such a trainer is intended to be used only as a training device and never itself as a drug delivery device.

Lavorini et al (2010) comment that two of the most critical patient errors in the uses of pMDI devices are a failure to coordinate inhalation with actuation of the device and inhaling the aerosolized drug too quickly. The full potential of the drug then cannot be realised.

Lavorini et al (2010) review various other inhaler training devices of different degrees of sophistication. However, each of these devices is a training device, in the sense that a patient uses the training device in order to "learn" an optimum method of using a drug delivery inhaler device. For the simplest devices, once the patient is deemed to have learned the correct technique, the training ends, but there is no ongoing check on whether the patient continues to use the correct technique, over time, with their prescribed drug delivery inhaler device.

Corrigan (2011) [C. J. Corrigan "Asthma therapy: there are guideline, and then there is real life . . . " Primary Care Respiratory Journal (2011) 20(1) 13-14] and Hardwell et al (2011) [A. Hardwell, V. Barber, T. Hargadon, E. McKnight, J. Holmes and M. L. Levy "Technique training does not improve the ability of most patients to use pressurised metered-dose inhalers (pMDIs)" Primary Care Respiratory Journal (2011) 20(1) 92-96] report on tests of patient compliance using pMDI devices. The tests took place during April-June 2008. The commentary in Corrigan (2011) on the results reported by Hardwell (2011) discusses the fact that 85.6% of 1291 patients tested failed their first assessment of whether they were able to use their pMDI device correctly. This is considered to be a critical issue—incorrect use of a pMDI device based on this assessment means that the drug delivered to the patient is being delivered sub-optimally. In turn, this means that the patient does not receive the correct dose of the drug, which can lead to serious problems in the ongoing treatment of conditions such as asthma. It is considered that such problems remain even when patients have in the past received some training on the correct technique to adopt for using their prescribed drug delivery inhaler device.

SUMMARY OF THE INVENTION

The present invention has been devised in order to address at least one of the above problems. Preferably, the present invention reduces, ameliorates, avoids or overcomes at least one of the above problems.

Accordingly, in a first aspect, the present invention provides an adapter for fitting to a drug delivery device, said adapter comprising:
  an outlet for communication with the mouth of a patient;
  an air flow path through the adapter along which air is drawn to the outlet by inhalation by the patient;
  an inlet adapted for connection to a mouthpiece of said drug delivery device; and
  an air flow rate indicator operable to indicate when the air flow rate along the air flow path is at or above a predetermined minimum level suitable for delivery of the drug to the patient.

In a second aspect, the present invention provides a use of a drug delivery inhaler device to deliver a drug to a patient by inhalation, the method comprising:
  connecting the inlet of an adapter according to the first aspect to the mouthpiece of the drug delivery device;
  the patient inhaling through the outlet of the adapter and thereby establishing an air flow along the air flow path through the adapter and device;
  the air flow rate indicator in the adapter providing an indication to the patient when the air flow rate along the air flow path is at or above a predetermined minimum level suitable for delivery of the drug to the patient; and
  while the air flow rate indicator provides said indication, operating a drug reservoir seated in the device to deliver a dose of aerosolized drug into the air flow path in the device for inhalation by the patient at the adapter outlet.

In a third aspect, the present invention provides a medicament for treatment of asthma and/or chronic obstructive pulmonary disease (COPD) in a patient, the medicament delivered to the patient by inhalation using a drug delivery inhaler device by the steps:
  connecting the inlet of an adapter according to the first aspect to the mouthpiece of the drug delivery device;
  the patient inhaling through the outlet of the adapter and thereby establishing an air flow along an air flow path through the adapter and device;
  an air flow rate indicator in the adapter providing an indication to the patient when the air flow rate along the air flow path is at or above a predetermined minimum level suitable for delivery of the drug to the patient; and
  while the air flow rate indicator provides said indication, operating a drug reservoir seated in the device to deliver a dose of aerosolized drug into the air flow path in the device for inhalation by the patient.

In this aspect the medicament is preferably one or more selected from the group consisting of: bronchodilators such as $\beta_2$-adrenoceptor agonists (e.g. salbutamol, terbutaline, salmeterol, formoterol) and anticholinergics (e.g. ipratropium bromide, tiotropium); glucocorticoids (e.g. prednisolone, fluticasone, budesonide, mometasone, beclomethasone); theophylline; phosphodiesterase-4 antagonists (e.g. roflumilast, cilomilast); tumor necrosis factor antagonists (e.g. infliximab); leukotriene antagonists (e.g. zafirlukast); mast cell stabilizers (e.g. cromolyn sodium).

Accordingly, in a fourth preferred aspect, the present invention provides a drug delivery inhaler device having:
an outlet for communication with the mouth of a patient;
an air flow path through the device along which air is drawn to the outlet by inhalation by the patient;
a seat for location of a drug reservoir, the drug reservoir being operable to deliver a dose of aerosolized drug into the air flow path for inhalation by the patient; and
an air flow rate indicator operable to indicate when the air flow rate along the air flow path is at or above a predetermined minimum level suitable for delivery of the drug to the patient.

In a fifth preferred aspect, the present invention provides a use of a drug delivery inhaler device to deliver a drug to a patient by inhalation, the method comprising:
the patient inhaling through an outlet of the device and thereby establishing an air flow along an air flow path through the device;
an air flow rate indicator providing an indication to the patient when the air flow rate along the air flow path is at or above a predetermined minimum level suitable for delivery of the drug to the patient; and
while the air flow rate indicator provides said indication, operating a drug reservoir seated in the device to deliver a dose of aerosolized drug into the air flow path for inhalation by the patient.

In a sixth preferred aspect, the present invention provides a medicament for treatment of asthma and/or chronic obstructive pulmonary disease (COPD) in a patient, the medicament delivered to the patient by inhalation using a drug delivery inhaler device by the steps:
the patient inhaling through an outlet of the device and thereby establishing an air flow along an air flow path through the device;
an air flow rate indicator providing an indication to the patient when the air flow rate along the air flow path is at or above a predetermined minimum level suitable for delivery of the drug to the patient; and
while the air flow rate indicator provides said indication, operating a drug reservoir seated in the device to deliver a dose of aerosolized drug into the air flow path for inhalation by the patient.

In this aspect, the medicament is preferably one or more selected from the group consisting of: bronchodilators such as $\beta_2$-adrenoceptor agonists (e.g. salbutamol, terbutaline, salmeterol, formoterol) and anticholinergics (e.g. ipratropium bromide, tiotropium); glucocorticoids (e.g. prednisolone, fluticasone, budesonide, mometasone, beclomethasone); theophylline; phosphodiesterase-4 antagonists (e.g. roflumilast, cilomilast); tumor necrosis factor antagonists (e.g. infliximab); leukotriene antagonists (e.g. zafirlukast); mast cell stabilizers (e.g. cromolyn sodium).

All aspects of the invention may have any one or, to the extent that they are compatible, any combination of the following optional features.

Preferably, the adapter in the first, second and third aspects is a substantially cylindrical tube (i.e. having a substantially constant cross-sectional area) unlike typical inhaler spacers. Preferably, the outlet of the adapter is adapted for connection to the mouthpiece of a drug delivery device by the inclusion of a press-fitting connection. The press/push-fitting connection is adapted to form an interference fit with the outlet/mouthpiece of the drug delivery device. The outlet of the adapter is adapted to form an air-tight seal upon connection with the mouthpiece/outlet of the drug delivery device.

Preferably, the drug delivery inhaler device is a pressurised metered dose inhaler (pMDI) device. In such devices, the drug is typically provided in the form of a liquid held in a pressurised canister. Actuation of the canister is typically achieved by depressing the canister towards the body of the device. This causes an interaction between the canister and the seat that causes a metered dose of liquid to be ejected from the canister, along with a propellant gas. The liquid is aerosolized in the device, for inhalation by the patient. A drug of particular interest is salbutamol, marketed under the trade names Ventolin™, Aerolin™, Ventorlin™, Asthalin™ Asthavent™, Proventil™ and ProAir™, for the management of asthma.

Pressurised metered dose inhaler (pMDI) devices typically have a body portion substantially in an L-shape, with the upright of the L having an inlet adapted to receive the drug reservoir and the transverse of the L providing an outlet (mouthpiece) for communication with the mouth of the patient.

Preferably, the predetermined minimum air flow rate through the device is at least 30 liters per minute. Preferably, the predetermined minimum air flow rate through the device is at most 60 liters per minute. As will be appreciated, the preferred range of air flow through the device in order to ensure satisfactory delivery of the drug to the patient is 30-60 liters per minute. A slower air flow rate risks that the aerosol particles will settle before being delivered to the required anatomy of the patient (typically to the bronchial tubes, and/or deeper into the lungs). A higher air flow rate risks the aerosol particles simply hitting and adhering to the back of the patient's throat, without penetrating deeper into the patient's pulmonary system.

In the fourth to sixth aspects, the air flow rate indicator may be provided in a body portion of the inhaler. This is advantageous, since it allows the indicator to be formed integrally with the body portion of the inhaler, and thus need not increase the overall size of the inhaler.

In the first, second and third aspects, the air flow rate indicator is provided in the adapter. This is advantageous in that, although the use of such an adapter increases the overall size of the device when in use, it allows a suitable air flow rate indicator to be retrofitted to an existing inhaler. The adapter may increase the distance between the drug reservoir and the mouth of the patient.

The air flow path through the device can be considered in two sections, relative to a drug injection/ejection point in the air flow path at which point the drug reservoir ejects drug into the air flow. An inlet region of the air flow path is typically located upstream of the drug injection point and leads to the air inlet of the device. An outlet region is typically located downstream of the drug injection point and leads to the outlet (mouthpiece) of the device. In the fourth to sixth aspects, the air flow rate indicator may be provided in the inlet region of the air flow path i.e. upstream of the point at which the drug is ejected from the reservoir into the air flow path. For example, the air flow rate indicator may be provided adjacent the drug reservoir. Alternatively, the air flow rate indicator may be provided in the outlet region of the device i.e. downstream of the point at which the drug is ejected from the reservoir into the air flow path.

In some embodiments of the first to sixth aspects, the air flow rate indicator generates an audible signal. For example, the air flow rate indicator may be a pressure-driven mechanical oscillator, such as a reed. Alternatively, the air flow rate indicator may be a whistle.

In some embodiments of the first to sixth aspects, the air flow rate indicator generates a visual signal. For example, air flow rate indicator may have a mechanically-operated signal such as a vane moveable in response to a pressure difference across it. In preferred embodiments, of the fourth to sixth aspects, the air flow rate indicator is adapted to generate a visual signal and is provided at the air inlet of the drug delivery device.

In some embodiments of the first to sixth aspects, the air flow rate indicator may operate electronically. Electronic air flow rate sensors are known, e.g. based on Venturi sensors. In the case of an electronic air flow rate indicator, the patient may be alerted to the air flow rate by a suitable signal such as an audible signal, a visual signal, or a combination of audible and visual signals. The audible and/or visual signal may be generated electronically.

Further optional features of the invention are set out below.

BRIEF DESCRIPTION OF THE DRAWINGS

Embodiments of the invention will now be described by way of example with reference to the accompanying drawings in which:

FIGS. 1-3 show various schematic views of an adapter according to the first aspect of the invention;

FIGS. 4-6 show various schematic views of a pMDI device according to an embodiment of the fourth aspect of the invention;

FIGS. 10-12 show various schematic views of a pMDI device according to a further embodiment of the fourth aspect of the invention.

Figure 9:
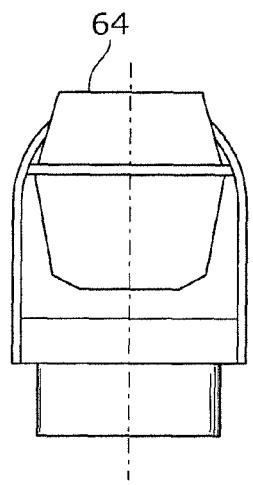
FIGS. 7-9 show various schematic views of a pMDI device according to another embodiment of the fourth aspect of the invention.

DETAILED DESCRIPTION OF PREFERRED EMBODIMENTS, AND FURTHER OPTIONAL FEATURES OF THE INVENTION

Pressurised metered dose inhaler (pMDI) devices typically have a body portion substantially in an L-shape, with the upright of the L adapted to receive a drug reservoir and the transverse of the L providing an outlet for communication with the mouth of the patient.

The drug is typically provided in the form of a liquid held in a pressurised canister. Actuation of the canister is typically achieved by depressing the canister towards the body of the device. This causes an interaction between the canister and the seat that causes a metered dose of liquid to be ejected from the canister, along with a propellant gas. The liquid is aerosolized in the device, for inhalation by the patient. A suitable drug for use in a pMDI device is salbutamol, which is well known for its use for the relief of bronchospasm in conditions such as asthma and COPD.

As discussed above, Corrigan (2011) and Hardwell et al (2011) show that around 85% of patients fail to use a pMDI correctly. In particular, this misuse relates to the timing of actuation of the drug canister and the inhalation rate.

Therefore the preferred embodiments of the invention provide an indication to the patient, when using the pMDI device itself, of when to actuate the drug canister, based on the air flow rate through the device.

FIGS. 1-3 show various views of an adapter according to an embodiment of the first aspect of the invention, in which the adapter is to be attached to a known pMDI device (not shown).

The adapter takes of the form of tube 10 moulded from plastics material. Tube 10 is open at each end 12, 14 and has a substantially constant internal cross sectional area, unlike known spacer devices. End 12 is for sealing attachment to an outlet of a known pMDI device. Different adapters 10 can be manufactured to be specific fits for various known pMDI devices. End 14 is for the user to place their mouth around and inhale, drawing air through the pMDI device. An air flow rate indicator, in the form of audible indicator 16, is provided in the side wall of the tube 10. In this embodiment, the audible indicator is a reed held at one end in an aperture in the side wall of tube 10. The reed resonates when a predetermined pressure difference is established across the aperture. Such a pressure difference is established by the patient inhaling. Thus, the predetermined pressure difference can be tuned by suitable selection of the reed and aperture characteristics so that the reed resonates and produces an audible signal when the air flow rate through the tube (and thus through the pMDI device) reaches a predetermined level of, e.g. 30 liters per minute. This informs that patient that a suitable air flow rate has been produced, so that the patient can activate the drug canister to deliver the metered dose of drug.

FIGS. 4-6 show various views of a pMDI device 20 according to an embodiment of the fourth aspect of the present invention. Device 20 operates in a similar manner to the embodiment of FIGS. 1-3, except that here the air flow rate indicator 34 is provided integrally with the body of the pMDI device.

With reference to FIG. 4, the pMDI device has a plastic body portion 22 in an L-shape. The upright of the L-shape is hollow and shaped to receive drug canister 24. The top end of drug canister 24 stands proud of the end of the body portion 22. At the base of the drug canister is provided a drug delivery port 26 located in seat 28. Upon depression of the canister 24, the drug delivery port is actuated to deliver a metered dose of the liquid drug held in the canister, along with a gaseous propellant. This mixture is forced through aperture 30 in such a manner that an aerosol of the drug is formed.

The user's mouth is received around outlet 32, which forms the transverse of the L-shape of the plastic body portion 22.

When the user inhales, an air flow is established through the device. Air (shown by arrows A in FIG. 4) is drawn into the device through the gap defined between the canister 24 and the body portion 22. There is therefore a significant constriction along the air flow path. Therefore the patient inhaling causes a pressure drop in the air flow path.

In a similar manner to that shown in FIGS. 1-3, an air flow rate indicator (in this case an audible indicator) is provided in the device of FIGS. 4-6. This audible indicator operates in a similar manner to that described with reference to FIGS. 1-3. In FIGS. 4-6, the audible indicator is located in the inlet region of the air flow path. However, this has no deleterious effect on the operation of the device—the audible indicator is designed in order to generate an audible signal when the air flow rate through the device reaches a predetermined level, such as 30 liters per minute.

In use, the patient starts to inhale slowly through the pMDI device. The patient gradually increases the rate of inhalation. When the air flow rate reaches the predetermined minimum flow rate, the audible indicator emits an audible signal (e.g. a constant tone) to the patient, and continues to do so even if the air flow rate increases slightly further (e.g. up to about 60 liters per minute). Once the patient hears the audible signal, the patient actuates the drug canister by depressing it, generating the drug aerosol and inhaling the aerosol via the outlet of the device at or near an optimal inhalation rate. In this way, the efficacy of the dose of drug is improved, and preferably maximised. This allows the drug to be delivered repeatably and at maximum benefit for the patient.

Figure 7:
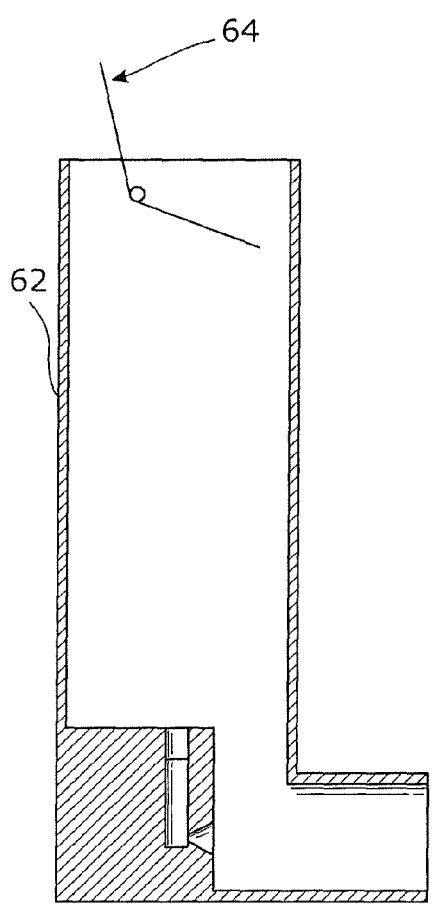
Figure 8:
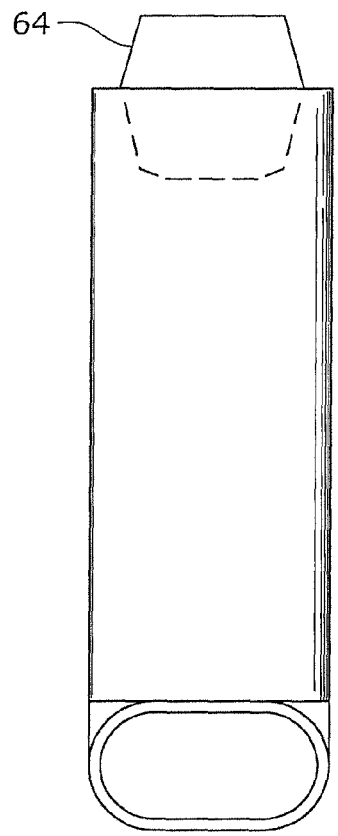

FIGS. 7-9 show various views of a pMDI device according to another embodiment of the invention. Compared with FIGS. 4-6, the drug canister is not shown, but it would be present in normal use.

If FIG. 7, the plastic body portion 62 has a similar overall shape to that shown in FIG. 4. However, there is no audible indicator in the device of FIG. 7. Instead, the air flow rate indicator is in the form of a visual indicator. The visual indicator is a hinged flap 64, located at the inlet to the air flow path of the device. At the predetermined air flow rate, the flap changes position, moving against a restoring force (e.g. gravity, or the restoring force of a spring (not shown)). This indicates to the patient that the minimum air flow rate has been achieved, and thus the drug canister (not shown) can be actuated to deliver the metered dose of drug.

FIGS. 10-12 show various views of a pMDI device according to a further embodiment of the invention. The overall construction of the device is similar to that shown in FIGS. 4-6, including the location of canister 24. However, as shown in FIG. 10, instead of an audible reed or whistle, there is instead provided an air flow rate sensor 80, located just upstream of the outlet of the device. As the skilled person will know, there are various suitable sensors that can be used. For example, a flow rate sensor may operate according to the Venturi effect, with a suitable combination of pressure sensors and circuitry to relate the pressure difference due the Venturi effect with the air flow rate through the flow rate sensor. Based on the output of the flow rate sensor 80, suitable circuitry is provided in order to provide an indication to the patient. For example, indicator arrangement 82 may provide visual indication (e.g. an LED display) and/or audible indication (e.g. a suitable tone or audible instruction).

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

What is claimed is:

1. A drug delivery inhaler device having:
   an L-shaped body with an upright portion for housing a drug reservoir and terminating at an air inlet and a transverse portion terminating at an outlet for communication with the mouth of a patient;
   an air flow path through the device along which air is drawn from the air inlet of the upright portion of the body to the outlet by inhalation by the patient;
   a seat for location of a drug reservoir, the drug reservoir being operable to deliver a dose of aerosolized drug into the air flow path for inhalation by the patient; and
   an air flow rate indicator operable to continuously indicate when the air flow rate along the air flow path is at or above a predetermined minimum level suitable for delivery of the drug to the patient both before and during delivery of the drug,
   wherein said air flow indicator is provided integrally with the upright portion of the body of the device upstream from the point at which the dose of aerosolized drug is ejected into the air flow path.

2. The drug delivery inhaler device according to claim 1, wherein the device is one of: a pressurised metered dose inhaler (pMDI) device, and a dry powder inhaler (DPI) device.

3. The drug delivery inhaler device according to claim 1, wherein the predetermined minimum air flow rate through the device is at least 30 liters per minute.

4. The drug delivery inhaler device according to claim 1, wherein the air flow rate indicator is adapted to generate an audible or visual signal.

5. The drug delivery inhaler device according to claim 1, wherein the air flow rate indicator is operable electronically.

6. The drug delivery inhaler device of claim 1, wherein the air flow rate indicator comprises a reed configured to oscillate to generate an audible signal.

7. The drug delivery inhaler device of claim 6, wherein the reed is disposed in an aperture in a side wall of the L-shaped body.

8. The drug delivery inhaler device of claim 1, wherein, in use, the air flow rate indicator is configured to be positioned upstream of a base of the drug reservoir and downstream of a top end of the drug reservoir in the air flow path.

9. The drug delivery inhaler device of claim 1, wherein said air flow rate indicator is adapted to be retrofitted to the drug delivery inhaler device.

10. A drug delivery inhaler device having:
    an L-shaped body with an upright portion configured for receiving a drug reservoir and terminating at an air inlet and a transverse portion terminating at an outlet for communication with the mouth of a patient;
    an air flow path through the device along which air is drawn from the air inlet of the upright portion of the body to the outlet by inhalation by the patient; and
    an air flow rate indicator operable to continuously indicate when the air flow rate along the air flow path is at or above a predetermined minimum level suitable for delivery of an aerosolized drug to the patient both before and during delivery of the drug,
    wherein said air flow indicator is provided integrally with the upright portion of the body of the device.

11. The drug delivery inhaler device according to claim 10, wherein the device is one of: a pressurised metered dose inhaler (pMDI) device, and a dry powder inhaler (DPI) device.

12. The drug delivery inhaler device according to claim 10, wherein the predetermined minimum air flow rate through the device is at least 30 liters per minute.

13. The drug delivery inhaler device according to claim 10, wherein the air flow rate indicator is adapted to generate an audible or visual signal.

14. The drug delivery inhaler device according to claim 10, wherein the air flow rate indicator is operable electronically.

15. The drug delivery inhaler device of claim 10, wherein the air flow rate indicator comprises a reed configured to oscillate to generate an audible signal.

16. The drug delivery inhaler device of claim 15, wherein the reed is disposed in an aperture in a side wall of the L-shaped body.

17. The drug delivery inhaler device of claim 10, wherein, in use, the air flow rate indicator is configured to be positioned upstream of a base of the drug reservoir and downstream of a top end of the drug reservoir in the air flow path.

18. The drug delivery inhaler device of claim 10, wherein said air flow rate indicator is adapted to be retrofitted to the drug delivery inhaler device.

19. A drug delivery inhaler device having:
- an L-shaped body with an upright portion configured for receiving a drug reservoir and terminating at an air inlet and a transverse portion terminating at an outlet for communication with the mouth of a patient;
- an air flow path through the device along which air is drawn from the air inlet of the upright portion of the body to the outlet by inhalation by the patient; and
- an air flow rate indicator operable to continuously indicate when the air flow rate along the air flow path is at or above a predetermined minimum level suitable for delivery of an aerosolized drug to the patient both before and during delivery of the drug; and said air flow indicator is provided in the air flow path at or proximate the air inlet of the upright portion of the body, wherein said air flow rate indicator is adapted to be retrofitted to the drug inhaler delivery device.

20. A drug delivery inhaler device having:
- an L-shaped body with an upright portion for housing a drug reservoir and terminating at an air inlet and a transverse portion terminating at an outlet for communication with the mouth of a patient;
- an air flow path through the device along which air is drawn from the air inlet of the upright portion of the body to the outlet by inhalation by the patient;
- a seat for location of a drug reservoir, the drug reservoir being operable to deliver a dose of aerosolized drug into the air flow path for inhalation by the patient; and
- an air flow rate indicator operable to continuously indicate when the air flow rate along the air flow path is at or above a predetermined minimum level suitable for delivery of the drug to the patient both before and during delivery of the drug, wherein said air flow indicator is provided within the upright portion of the body of the device, upstream from the point at which the dose of aerosolized drug is ejected into the air flow path.

* * * * *